(12) United States Patent
Salituro et al.

(10) Patent No.: US 7,037,688 B2
(45) Date of Patent: May 2, 2006

(54) METHOD FOR USING UNEQUAL PRIMER CONCENTRATIONS FOR GENERATING NUCLEIC ACID AMPLIFICATION PRODUCTS

(75) Inventors: John A. Salituro, Racine, WI (US); John J. Carrino, San Diego, CA (US)

(73) Assignee: Abbott Laboratories, Abbott Park, IL (US)

( * ) Notice: Subject to any disclaimer, the term of this patent is extended or adjusted under 35 U.S.C. 154(b) by 354 days.

(21) Appl. No.: 10/097,997

(22) Filed: Mar. 14, 2002

(65) Prior Publication Data

US 2002/0160406 A1    Oct. 31, 2002

Related U.S. Application Data

(63) Continuation of application No. 09/079,675, filed on May 15, 1998, now Pat. No. 6,391,544.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/91.2; 435/6; 435/91.1; 435/183; 536/23.1; 536/24.31; 536/24.33

(58) Field of Classification Search ............ 435/6, 435/91.1, 91.2, 183; 436/94; 536/23.1, 536/24.31, 24.33
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,948,882 A | 8/1990 | Ruth | |
| 5,066,584 A | 11/1991 | Gyllensten | |
| 5,424,414 A | 6/1995 | Mattingly | |
| 5,453,361 A * | 9/1995 | Yancopoulos et al. | 435/69.1 |
| 5,464,746 A | 11/1995 | Fino | |
| 5,610,017 A | 3/1997 | Gudibande et al. | |
| 5,629,158 A | 5/1997 | Uhlenm | |
| 5,710,029 A * | 1/1998 | Ryder et al. | 435/6 |
| 5,763,174 A * | 6/1998 | Nishikura | 435/6 |
| 5,837,293 A * | 11/1998 | De Waal Malefyt et al. | 424/85.2 |
| 6,391,544 B1 * | 5/2002 | Salituro et al. | 435/6 |

FOREIGN PATENT DOCUMENTS

| | | |
|---|---|---|
| DE | 19808534 | 9/1999 |
| EP | 0418960 | 3/1991 |
| WO | 9003444 | 4/1990 |
| WO | 9424307 | 10/1994 |
| WO | 9943849 | 9/1999 |

OTHER PUBLICATIONS

Eliaou, J. et al. "Generic HLA-DRBI Gene Oligotyping by a Nonradioactive Reverse Dot-Blot Methodology", Human Immunology, USA, vol. 35. pp. 215-222. (Dec. 1992.
McCabe, P. "Production of Single-Stranded DNA by Asymmetric PCR" PCR Protocols: A Guide to Methods and Applications, Academic Press, USA, pp. 76-83. (1990).
"Gene Charecterization Kits" Stratagen Catalog. 1998 Edition, pp. 39.

* cited by examiner

*Primary Examiner*—Bradley L. Sisson

(57) ABSTRACT

The method provided herein is a method for detecting a target sequence in a test sample. Generally, the method comprises forming a reaction mixture comprising a test sample, amplification reagents, a first primer, and a second primer wherein the concentration of the first primer in the reaction mixture is 15% to 250% percent greater than the concentration of the second primer. The target sequence is amplified according to any amplification protocol that employs the primer sequences to generate copies of the target sequence that include a product from the first and second primers. A probe is hybridized to the amplification product from the first primer to form a hybrid complex; and the hybrid complex is detected as an indication of the presence of the target sequence in the test sample.

4 Claims, No Drawings

METHOD FOR USING UNEQUAL PRIMER CONCENTRATIONS FOR GENERATING NUCLEIC ACID AMPLIFICATION PRODUCTS

This application is a continuation of U.S. application Ser. No. 09/079,675, filed May 15, 1998 now U.S. Pat. No. 6,391,544.

TECHNICAL FIELD OF THE INVENTION

The present invention relates to nucleic acid amplification reactions and in particular relates to amplification reactions that employ a pair of primer sequences to generate copies of a target sequence.

BACKGROUND OF THE INVENTION

Nucleic acid amplification reactions are well known and are employed to increase the concentration of a target nucleic acid in a test sample. The "target nucleic acid" typically is present in a sample in low concentrations and therefore cannot easily be detected without amplifying it to increase the concentration of the target sequence in the sample. The polymerase chain reaction (PCR) is one nucleic acid amplification reaction commonly employed for purposes of amplifying a target nucleic acid sequence.

According to the principles of PCR, "primer sequences" are used to prime synthesis of copies of the target sequence. Specifically, under appropriate conditions, primer sequences hybridize to opposite strands of a double stranded nucleic acid sequence such that the primers flank the target sequence. Once hybridized, the primers are extended using enzymes such as, for example, DNA polymerase which extend the primer sequences to thereby generate copies of the target sequence. Additional copies of the target sequence are generated by cycling the above steps of (i) hybridizing and extending the primer sequences and (ii) dissociating the extended primer sequences (or copies of the target sequence) so that additional primers can hybridize to the original target, as well as copies of the target sequence. Hence, multiple copies of the target sequence are generated.

Once amplified, copies of the target sequence can be detected to determine if the target sequence originally was present in the test sample. Of course, if the target sequence was not present, amplification should not occur and the target sequence should not be detected. In any event, amplified target sequences are typically detected using labels. Labels are moieties that have a detectable property and can be incorporated into the copies of the target sequence. Labels typically are incorporated into the amplified target sequences by attaching the labels to primer sequences that are then incorporated into the amplification product as specified above. Alternatively, for example, extension products can be labeled by incorporating labeled nucleotides into such products during primer extension. The presence of the target sequence in the test sample can then be determined by detecting the labeled amplification product.

Amplified target sequences also can be detected using labeled probes that hybridize to a strand or both strands of an amplified target sequence. However, it is sometimes desirable to employ a probe that hybridizes to only one strand of a double stranded amplification product. The effect of such a detection scheme, at least as it applies to a double stranded target sequence, is that a single strand of amplified target sequence is detected to determine the presence of the target sequence in the test sample. However, detecting a single strand of an amplification product can be inefficient insofar as the signal plateaus and sometimes drops (or hooks) as the number of target sequences originally present in the test sample increases. Alleviating the "hooking" or "plateauing" phenomenon and providing a linear signal over a broader range of target sequence concentrations would be beneficial, especially for amplification based assays designed to quantify the amount of a target sequence in a test sample.

It would be expected that substantially increasing the concentration of one primer over the other would alleviate this problem by generating more of the sequence that is detected. Indeed, U.S. Pat. No. 5,066,584 describes a method for preferentially generating one strand of a double stranded target sequence by vastly increasing the concentration of one primer. However, this requires excess reagents and therefore excess costs associated with preferentially producing one of two single strands. Additionally, substantially increasing primer concentrations may increase the chances of non-specific priming and therefore amplification of non-target sequences. Moreover, many times, competing non-specific reactions will interfere with the efficient amplification of the sequence of interest. Therefore, it may be expected that substantially increasing the concentration of one primer over the other primer may present problems in amplification assays designed to be of high sensitivity (i.e. designed to detect low numbers of a sequence of interest).

SUMMARY OF THE INVENTION

The present invention provides a method of detecting a target sequence in a test sample. The method comprises the steps of: (a) forming a reaction mixture comprising a test sample, amplification reagents, a first primer, and a second primer such that the concentration of the first primer in the reaction mixture is 15% to 250% percent greater than the concentration of the second primer; (b) amplifying the target sequence to generate copies of the target sequence comprising an amplification product from the first and second primers; (c) hybridizing a probe to the amplification product from the first primer to form a hybrid complex; and (d) detecting the hybrid complex as an indication of the presence of the target sequence in the test sample. Preferably, the hybrid complex is detected using labels that can either be directly detectable or indirectly detectable.

Also provided is an improved method for amplifying and detecting a target nucleic acid sequence in a test sample comprising the steps of: (a) forming an amplification mixture comprising a test sample, a first and a second primer sequence, and amplification reagents, (b) amplifying the target sequence to generate copies of the target sequence comprising an amplification product from the first and second primers; and (c) detecting the copies of the target sequence as an indication of the presence of the nucleic sequence in the test sample; wherein the improvement comprises providing the first primer sequence in 15% to 250% excess over the second primer and wherein a probe is hybridized to the amplification product from the first primer to form a hybrid complex and the hybrid complex is detected as an indication of the presence of the nucleic acid sequence in the test sample.

Kits for performing the methods of the invention are also provided.

DETAILED DESCRIPTION OF THE INVENTION

Under appropriate conditions, a primer pair will generate copies of a target sequence in the form of a double stranded amplification product. Unfortunately, however, when a single strand of a double stranded amplification product is detected with a probe, the resulting signal can plateau, or even hook, as the concentration of the original target sequence increases. To a certain extent, this phenomenon is counterintuitive since increasing the concentration of the original target sequence should yield a greater concentration of end product, and therefore, a greater signal should be detected. However, as mentioned above, the resulting signal can plateau. While not wishing to be bound by theory, the hooking effect may be attributable to the presence of higher concentrations of longer product strands driving product strand re-annealing to the exclusion of probe/target strand annealing. Applicants have surprisingly and unexpectedly discovered that the plateauing or hooking phenomenon could be alleviated by increasing the concentration of one primer so that it is slightly higher than the concentration of the other primer.

The method provided herein can be applied to any amplification reaction where a pair of primer sequences is employed to generate double stranded amplification products and only one strand of the double stranded products is detected. The method comprises a step where an amplification mixture is formed. The amplification mixture generally will comprise (i) a test sample, (ii) amplification reagents and (iii) a first and second primer (collectively referred to as a "primer pair"). As used herein, the term "test sample" means anything suspected of containing a target sequence. The test sample is or can be derived from any biological source, such as for example, blood, ocular lens fluid, cerebral spinal fluid, milk, ascites fluid, synovial fluid, peritoneal fluid, amniotic fluid, tissue, fermentation broths, cell cultures and the like. The test sample can be used directly as obtained from the source or following a pre-treatment to modify the character of the sample. Thus, the test sample can be pre-treated prior to use by, for example, preparing plasma from blood, disrupting cells or viral particles, preparing liquids from solid materials, diluting viscous fluids, filtering liquids, distilling liquids, concentrating liquids, inactivating interfering components, adding reagents, purifying nucleic acids, and the like. The "target sequence" that may be present in the test sample is a nucleic acid sequence that is amplified, detected, or amplified and detected. Additionally, while the term target sequence is sometimes referred to as single stranded, those skilled in the art will recognize that the target sequence may actually be double stranded.

The phrase "amplification reaction reagents" as used herein means reagents which are well known for their use in nucleic acid amplification reactions and may include but are not limited to: an enzyme or enzymes separately or individually having DNA polymerase and/or reverse transcriptase activity; enzyme cofactors such as magnesium or manganese; salts; nicotinamide adenine dinucleotide (NAD); deoxynucleoside triphosphates (dNTPs) such as, for example, deoxyadenosine triphosphate, deoxyguanosine triphosphate, deoxycytodine triphosphate and thymidine triphosphate; and an appropriate buffer.

The first and second primers typically are nucleic acid sequences, usually DNA or RNA. The length of the primers is not critical but primer sequences are usually about 10 to about 100 nucleotides long, preferably from about 15–35 nucleotides long, and have a defined base sequence suitable for hybridizing to the desired target sequence. Primer pairs usually are selected such that they flank the target sequence as is well known in the art. Additionally, the first primer is added to the amplification mixture such that its concentration is between 15% to 250% greater, and preferably 20% to 150% greater, than the concentration of the second primer. Of course, the first primer can be employed at concentrations of 400%, 500% and up to and more than 1000% greater than the concentration of the second primer, but as the concentration of one primer over the other increases, reagent costs and/or non-specific priming can become a limiting factor. In any event, upon hybridization of a primer to a target sequence, the primer is extended to generate a complement of the sequence to which the primer is hybridized.

Primer sequences can be from natural or synthetic sources and can routinely be synthesized using a variety of techniques currently available. For example, primers can be synthesized using conventional nucleotide phosphoramidite chemistry and instruments available from Perkin Elmer/Applied Biosystems, Div., (Foster City, Calif.) or Perceptive Biosystems, Inc., (Framingham, Mass.). If desired, a primer can be labeled using methodologies well known in the art such as described in U.S. Pat. Nos. 5,464,746; 5,424,414; and 4,948,882.

After the amplification mixture is formed, the target nucleic acid is amplified by subjecting reaction mixture to "amplification conditions" which are conditions that promote amplification of the target sequence. Amplification conditions are well known to those skilled in the art and generally comprise conditions that promote dissociation of a double stranded target sequences, annealing of the primer sequences to the single strands of the target sequence, and extension of the primer sequences to thereby form copies of the target sequences. The copies of the target sequence are then dissociated from the target and additional primer sequences are annealed to both the original target sequence and copies of the target sequence to thereby start a new round of amplification of the target sequence. Such amplification conditions are well known and have been described in U.S. Pat. Nos. 4,683,202 and 4,683,195 both of which are herein incorporated by reference. Thermal cycling is a preferred and well known method for producing amplification conditions. The number of times an amplification mixture is cycled is a matter of choice for one skilled in the art and typically, a reaction mixture is cycled between 2 and 100 times and more typically between 20 and 40 times.

After cycling, multiple copies of the target sequence may be present. The sequence(s) generated by the first primer is the sequence that is detected to indicate the presence of the target sequence in the test sample and this sequence synthesized by the first primer is variously referred to herein as the "primary sequence". Any method for detecting a single strand of a double stranded amplification product can be employed according to the present invention. For example, sequencing, gel electrophoresis, gel shift assays, solution hybridization assays, "TaqMan"like assays, and similar formats can be employed to detect the primary sequence.

According to a preferred detection embodiment, a hybridization probe is employed to detect the primary sequence, particularly when the probe is at relatively low concentrations. Probe sequences hybridize to the primary sequence to form a hybrid complex. Preferably, probes hybridize to the primary sequence in a region that is internal with respect to the primers. Formation of a hybrid complex between the primary sequence and probe can be accomplished by placing any double stranded target sequences under dissociation conditions followed by placing any resultant single stranded sequences under hybridization conditions in the presence of a probe. The phrase "dissociation conditions" is defined generally as conditions which promote dissociation of double stranded nucleic acid to the single stranded form. These conditions can include high temperature and/or low ionic strength. The phrase "hybridization conditions" is defined generally as conditions which promote nucleation and annealing of complementary nucleic acid sequences. It is well known in the art that such annealing and hybridization is dependent in a rather predictable manner on several parameters, including temperature, ionic strength, sequence length and G:C content of sequences. For any given set of sequences, melt temperature, or Tm, can be estimated by any of several known methods. Typically hybridization conditions include temperatures which are slightly below the melt temperature of given set of nucleic acid sequences. Ionic strength or "salt" concentration also impacts the melt temperature, since small cations tend to stabilize the formation of duplexes by shielding the negative charge on the phosphodiester backbone. Typical salt concentrations depend on the nature and valence of the cation but are readily understood by those skilled in the art. Similarly, high G:C content and increased sequence lengths are also known to stabilize duplex formation because G:C pairings involve 3 hydrogen bonds where A:T pairs have just two, and because longer sequences have more hydrogen bonds holding the strands together. Thus, a high G:C content and longer sequence length impact what "hybridization conditions" will encompass. Based upon the above, determining the proper "hybridization conditions" for a particular set of nucleic acid sequences is well within the ordinary skill in the art. U.S. patent application Ser. No. 08/514,704, filed Aug. 14, 1995, exemplifies a method of detecting amplified target sequences with a probe.

Probes are also nucleic acid sequences or nucleic acid analog sequences such as, for example, DNA, RNA, peptide nucleic acids, morpholino nucleic acids, that can be synthesized and labeled in the same manner that primer sequences are synthesized and labeled, as specified above. Selection of labels employed on a labeled primer or probe is a matter of choice for those skilled in the art and the term "label" as used herein refers to a molecule or moiety having a property or characteristic which is capable of detection. A label can be directly detectable, as with, for example, radioisotopes, fluorophores, chemiluminophores, enzymes, colloidal particles, fluorescent microparticles, FRET pairs, and the like. Alternatively, a label may be indirectly detectable, as with, for example, specific binding members. It will be understood that directly detectable labels may require additional components such as, for example, substrates, triggering reagents, light, and the like to enable detection of the label. When indirect labels are used for detection, they are typically used in combination with a conjugate as will be discussed further below.

Probes can be employed in a variety of ways, known in the art, to detect the primary sequence. For example, the probe, primer or probe and primer can be labeled and/or immobilized to solid support materials to detect the presence of the primary sequence. Capture reahents also can be employed to aid in detecting a primary sequence. A "capture reagent" as used herein means a specific binding menber attached to a solid support material. "Specific binding member" as used herein, means a ember of a specific biding pair, i.e. two different molecules where one of the molecules through, for example, chemical or physical means specifically binds to the other molecule. In addition to antigen and antibody specific binding pairs, other specific binding pairs include, but are not intended to be limited to avidin and biotin; complementary nucleotide sequences; haptens and antibodies specific for haptens such as carbazole and adamantane described in U.S. Pat. Nos. 5,424,414 and 5,464,746, respectively; and the like. A "solid support material", refers to any material which is insoluble, or can be made insoluble by a subsequent reaction. Solid support materials thus can be latex, plastic, derivatives plastic, magnetic or non-magnetic metal , glass, silicon or the like. A vast array of solid support material configurations are also well known and include, but are not intended to be limited to, surfaces of rest tubes, microtiter wells, sheets, beads, microparticles, chips and other configurations well know to those skilled in the art.

According to one embodiment for detecting a primary sequence using a probe, the probe can be immobilized to a solid support material to form a capture reagent. The primary sequence can be contacted with the so-formed capture reagent under hybridization conditions to form a hybrid complex and thereby capture the primary sequence and, if desired, separate it from other amplification reactants and products. A signal from a label attached to the primary sequence can then be detected as an indication of the presence of the primary sequence on the capture reagent and therefore in the test sample.

As a further alternative, the first primer and probe can be labeled and the primary sequence can be separated and detected using such labels. For example, both labels of such a configuration can be specific binding members. Hence upon formation of a hybrid complex, the complex will be bi-labeled. One label can bind to a specific binding member on a capture reagent that permits separation of the hybrid complex and the other label can be used to bind a conjugate which can be employed to detect the presence of the hybrid complex on the capture reagent. The term "conjugate" as used herein means a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label.

EXAMPLES

The following examples demonstrate detection of HIV nucleic acid using the DNA oligomer primers and probes herein provided. These DNA primers and probes are identified as SEQUENCE ID NO. 2, SEQUENCE ID NO. 3 and SEQUENCE ID NO. 4 and are specific for a region in the pol gene of HIV. A portion of a representative pol sequence from HIV-1 (subtype B, strain MN) is designated herein as SEQ ID NO. 1. These primers and probes are consensus sequences derived from analysis of the pol region of 31 HIV-1 isolates, representing subtypes A through F and O of HIV-1.

In the following examples, SEQ ID NO. 2 and SEQ ID NO. 3 are used as consensus amplification primers specific for the pol region of HIV-1. SEQ ID NO. 4 is used as a consensus internal hybridization probe for the HIV-1 pol amplification product.

Example 1

Preparation of HIV Primers and Probes

A. HIV Primers. Consensus primers were designed to detect the HIV pol target sequence of all known HIV-1 subtypes by oligonucleotide hybridization PCR. These primers were SEQ ID NO. 2 and SEQ ID NO. 3. Primer sequences were synthesized using standard oligonucleotide synthesis methodology, and SEQ ID NO. 3 was haptenated with carbazole at the 5' end using standard cyanoethyl phosphoramidite coupling chemistry as described in U.S. Pat. No. 5,424,414.

B. HIV Probes. The consensus probe, designated SEQ ID NO. 4, was designed to hybridize with the amplified HIV pol target sequences by oligonucleotide hybridization. The probe sequence was synthesized using standard oligonucleotide synthesis methodology and haptenated with 2 adamantanes at the 5' end using standard cyanoethyl phosphoramidite coupling chemistry as described in U.S. Pat. No. 5,464,746 and blocked with phosphate at the 3' end.

Example 2

Detection of HIV Varying the Unlabeled Primer Concentration

HIV RNA was isolated from a known quantity of virions (Advanced Biotechnologies Inc., Columbia, Md.) using RNAzol B RNA Isolation Solvent (Tel-Test, Inc., Friendswood, Tex.), extracted with chloroform/isopropanol and precipitated with ethanol. The pellet was resuspended in RNase-free water (5'-3', Boulder Colo.). Ten-fold dilutions of this HIV RNA were then prepared at concentrations of $10^6$ to $10^1$ RNA molecules/25 µl using a diluent containing 2 ng/µl of ribosomal RNA (rRNA; Boehringer-Mannheim, Indianapolis Ind.).

Dilutions of the HIV RNA (excluding $10^4$) were reverse transcribed, PCR amplified and detected using SEQ ID NOs. 2 and 3 as primers with SEQ ID NO. 4 as the HIV probe. RT-PCR was performed using 1×EZ Buffer, 2.5 mM manganese chloride, dNTPs (dATP, dGTP, dTTP and dCTP) present at a final concentration of 0.15 mM each, and recombinant *Thermus thermophilus* polymerase at a concentration of 5 units/reaction. The labeled primer (SEQ ID NO. 3) was used at a concentration of 50 nM and the unlabeled primer concentration was varied in separate reactions for each set of HIV RNA dilutions, using concentrations of 25, 37.5, 50 or 62.5 nM. The probe, which was labeled as specified above and that ultimately hybridizes with the product of the labeled primer prior to detection of the resultant hybrid complex, was used at a concentration of 10 nM. The ten-fold dilutions of HIV RNA in a sample volume of 25 µl were added to 175 µl containing the above mixtures for a total reaction volume of 0.2 ml. The negative control was composed of 50 ng of rRNA/reaction. All reactions were performed in duplicate.

Reaction mixtures were reverse transcribed and amplified in a Perkin-Elmer 480 Thermal Cycler. Reaction mixtures were first incubated at 62° C. for 30 minutes to reverse transcribe the RNA, followed by 2 minutes at 94° C. PCR amplification was then initiated through a touchdown or step-down protocol to aid in the stringency of the reaction in the early stages of amplification. This utilized 8 cycles as follows: 1 cycle at 94° C. for 30 seconds then 70° C. for 80 seconds followed by 1 cycle of 94° C. for 30 seconds then 69° C. for 80 seconds, followed by 1 cycle of 94° C. for 30 seconds then 68° C. for 80 seconds, followed by 1 cycle of 94° C. for 30 seconds then 67° C. for 80 seconds, followed by 1 cycle of 94° C. for 30 seconds then 66° C. for 80 seconds, followed by 1 cycle of 94° C. for 30 seconds then 65° C. for 80 seconds, followed by 1 cycle of 94° C. for 30 seconds then 64° C. for 80 seconds, followed by 1 cycle of 94° C. for 30 seconds then 63° C. for 80 seconds. Further amplification was then accomplished with 35 cycles at 94° C. for 30 seconds then 62° C. for 80 seconds. After the reaction mixtures were thermal cycled, all duplicates were pooled and mixed by pipetting to eliminate any variation due to cycling. The mixtures were then split and denatured for 5 minutes at 97° C. Following this, probe oligo hybridization was accomplished by lowering the temperature to 15° C. for 5 minutes The temperature was then lowered to 4° C. and samples were held at 4° C. until detection of reaction products.

Reaction products were detected on the Abbott LCx® system (available from Abbott Laboratories, Abbott Park, Ill.). A suspension of anti-carbazole antibody coated microparticles at 0.06% solids and an anti-adamantane antibody/alkaline phosphatase conjugate (all of which are commercially available from Abbott Laboratories, Abbott Park, Ill.) were used in conjunction with the LCx® to capture and detect the amplified product/probe hybrid. The enzyme substrate used was methyl-umbelliferyl phosphate (MUP), with the rate of conversion of MUP to MU measured and reported as counts/second/second (c/s/s).

Data from this experiment is presented in Table 1 and shows that when the unlabeled primer is present at concentrations below that of the labeled primer higher signals are achieved at higher target concentrations, and plateauing of the signal is avoided. Conversely, when the concentration of the unlabeled primer is higher than, or equal to, the concentration of the labeled primer, a "hook effect" is observed wherein a higher target concentration begins to give a lower signal.

TABLE 1

| HIV RNA | LCx ® Rate (c/s/s) Unlabeled Primer Concentration | | | |
|---|---|---|---|---|
| (molecules) | 25 nM | 37.5 nM | 50 nM | 62.5 nM |
| 0 | 28.2 | 26.7 | 26.5 | 24.1 |
| $10^1$ | 30.8 | 29.0 | 76.3 | 107.1 |
| $10^2$ | 39.2 | 78.6 | 190.5 | 299.7 |
| $10^3$ | 156.6 | 389.9 | 477.7 | 485.1 |
| $10^5$ | 1017.1 | 898.8 | 591.2 | 334.5 |
| $10^6$ | 1156.3 | 942.2 | 575.5 | 298.3 |

(Labeled primer was used at a concentration of 50 nM)

This experiment was also performed using a denaturation time of 15 minutes instead of 5 minutes, with equivalent results.

Example 3

Detection of HIV Varying the Labeled Primer Concentration

The same HIV RNA sample dilutions used in Example 2 were reverse transcribed, PCR amplified and detected as in Example 2 except two separate preparations (G and A) of unlabeled primer (SEQ ID NO. 2), both at 50 nM, were used and the concentration of the labeled primer (SEQ ID NO. 3) was varied in separate reactions for each HIV RNA dilution set, using 25, 50 and 75 nM of labeled primer. All reactions were performed in duplicate, with duplicate sets pooled after amplification and probe hybridization, to eliminate any variation due to cycling. Detection of reaction products utilized anti-carbazole antibody coated microparticles at 0.12% and 0.18% solids, in addition to the 0.06% solids used in Example 2. Results are shown below in Table 2.

TABLE 2

| HIV RNA | Unlabeled Primer G Labeled Primer Concentration | | | Unlabeled Primer A Labeled Primer Concentration | | |
|---|---|---|---|---|---|---|
| (Molecules) | 25 nM | 50 nM | 75 nM | 25 nM | 50 nM | 75 nM |
| LCx ® Rate (c/s/s) at 0.06% solids | | | | | | |
| 0 | 27.9 | 25.8 | 27.0 | 26.1 | 28.3 | 26.7 |
| $10^1$ | 78.5 | 77.4 | 40.2 | 70.6 | 59.2 | 90.6 |
| $10^2$ | 340.4 | 321.2 | 173.0 | 319.1 | 414.1 | 401.3 |
| $10^3$ | 391.0 | 553.1 | 574.0 | 179.7 | 561.1 | 750.1 |
| $10^5$ | 108.9 | 860.3 | 1035.5 | 34.1 | 442.7 | 1130.5 |
| $10^6$ | 47.4 | 903.8 | 1068.6 | 34.0 | 383.3 | 1139.8 |
| LCx ® Rate (c/s/s) at 0.12% solids | | | | | | |
| 0 | 57.7 | 53.6 | 52.0 | 56.8 | 56.5 | 53.6 |
| $10^1$ | 133.6 | 146.1 | 78.7 | 125.0 | 118.1 | 185.0 |
| $10^2$ | 465.0 | 498.9 | 312.5 | 461.1 | 613.0 | 615.0 |
| $10^3$ | 530.6 | 803.7 | 859.1 | 272.6 | 773.0 | 1008.3 |
| $10^5$ | 188.5 | 999.4 | 1272.7 | 69.9 | 581.4 | 1307.9 |
| $10^6$ | 90.3 | 1053.4 | 1289.2 | 67.0 | 512.9 | 1322.8 |
| LCx ® Rate (c/s/s) at 0.18% solids | | | | | | |
| 0 | 80.9 | 76.0 | 77.4 | 82.5 | 78.5 | 77.1 |
| $10^1$ | 156.9 | 176.9 | 101.4 | 147.3 | 139.6 | 226.0 |
| $10^2$ | 505.2 | 538.1 | 374.2 | 502.9 | 663.5 | 678.3 |
| $10^3$ | 568.5 | 830.6 | 911.7 | 326.9 | 830.5 | 1097.4 |
| $10^5$ | 237.2 | 1036.1 | 1296.5 | 98.9 | 617.2 | 1317.7 |
| $10^6$ | 117.9 | 1019.3 | 1321.6 | 93.4 | 544.4 | 1347.6 |

(Unlabeled primers G and A were used at a concentration of 50 nM)

The two unlabeled primer preparations (G and A) resulted in slightly different values but showed the same overall trends. In all cases, when the concentration of the unlabeled primer was higher than, or equal to, the concentration of the labeled primer, a "hook effect" was again seen, as in Example 2, wherein a high target concentration gave a low signal. Only when the unlabeled primer was present at concentrations lower than the labeled primer was a more linear signal produced correlating with target concentration. Under these conditions, as in Example 2, higher signals were again achieved at higher target concentrations, and plateauing of the signal was avoided.

Use of microparticle concentrations of 0.12% and 0.18% solids gave equivalent results, with both resulting in slightly higher signals than when 0.06% solids was used. However, changing the microparticle concentration did not affect the overall trends seen due to the ratio of unlabeled to labeled primer.

Example 4

Detection of HIV at Various Primer and Probe Concentrations

The same HIV RNA sample dilutions used in Example 2 were reverse transcribed, PCR amplified and detected as in Example 3 except the concentrations of both primers and probe were varied. The unlabeled primer (SEQ ID NO. 2) was used at concentrations between 100 and 250 nM, varying in 50 nM increments. The labeled primer (SEQ ID NO. 3) was used at concentrations between 50 and 500 nM, varying in 50 to 100 nM increments. The probe was used at concentrations of 10, 25 and 40 nM, with the various primer concentrations as indicated in Table 3.

TABLE 3

| HIV RNA | LCx ® Rate (c/s/s) at 0.12% solids unlabeled primer (nM)/labeled primer (nM)/probe (nM) | | | | | | | |
|---|---|---|---|---|---|---|---|---|
| (mol) | 100/50/10 | 100/100/10 | 100/150/10 | 100/200/10 | 150/100/10 | 150/150/10 | 150/200/10 | 150/300/10 |
| 0 | 48.2 | 50.3 | 46.1 | 44.0 | 48.2 | 44.8 | 46.1 | 45.0 |
| $10^1$ | 195.7 | 168.3 | 140.5 | 138.7 | 276.8 | 263.3 | 216.8 | 295.5 |
| $10^2$ | 551.8 | 599.3 | 606.5 | 578.3 | 594.6 | 611.1 | 795.0 | 569.1 |
| $10^3$ | 314.6 | 830.1 | 1074.2 | 988.0 | 828.8 | 881.9 | 900.7 | 865.8 |
| $10^5$ | 67.7 | 970.9 | 1200.7 | 1187.9 | 188.0 | 1061.0 | 1190.0 | 1020.2 |
| $10^6$ | 53.8 | 945.8 | 1214.1 | 1128.2 | 85.9 | 1021.8 | 1173.1 | 982.7 |
| | 200/150/10 | 200/200/10 | 200/250/10 | 200/400/10 | 250/200/10 | 250/250/10 | 250/300/10 | 250/500/10 |
| 0 | 42.2 | 44.8 | 43.6 | 40.9 | 45.2 | 44.9 | 48.1 | 39.3 |
| $10^1$ | 377.1 | 192.4 | 136.0 | 163.1 | 111.7 | 262.3 | 149.6 | 181.4 |
| $10^2$ | 569.3 | 710.7 | 620.1 | 486.1 | 655.2 | 558.8 | 558.8 | 600.5 |
| $10^3$ | 593.7 | 850.2 | 848.7 | 779.7 | 797.7 | 808.3 | 844.9 | 820.4 |
| $10^5$ | 302.1 | 958.0 | 1080.3 | 888.8 | 734.0 | 963.9 | 1072.8 | 930.0 |
| $10^6$ | 198.6 | 1050.5 | 1161.3 | 913.8 | 463.8 | 1018.2 | 1174.2 | 944.9 |
| | 100/150/25 | 100/200/25 | 150/200/25 | 150/300/25 | 200/250/25 | 200/400/25 | 250/300/25 | 250/500/25 |
| 0 | 47.6 | 47.8 | 47.9 | 46.3 | 44.7 | 45.7 | 44.8 | 46.0 |

TABLE 3-continued

| HIV RNA | LCx ® Rate (c/s/s) at 0.12% solids unlabeled primer (nM)/labeled primer (nM)/probe (nM) | | | | | | | |
|---|---|---|---|---|---|---|---|---|
| (mol) | 100/50/10 | 100/100/10 | 100/150/10 | 100/200/10 | 150/100/10 | 150/150/10 | 150/200/10 | 150/300/10 |
| $10^1$ | 211.1 | 239.0 | 244.3 | 209.9 | 184.4 | 204.2 | 189.4 | 92.2 |
| $10^2$ | 929.0 | 618.5 | 484.3 | 638.0 | 713.5 | 643.2 | 1020.1 | 608.3 |
| $10^3$ | 1175.3 | 1206.0 | 1049.0 | 1167.7 | 977.8 | 1045.3 | 992.4 | 1015.4 |
| $10^5$ | 1619.4 | 1575.2 | 1507.0 | 1392.9 | 1320.6 | 1162.9 | 1204.6 | 1106.8 |
| $10^6$ | 1620.8 | 1610.2 | 1551.3 | 1328.6 | 1412.3 | 1194.0 | 1362.4 | 1152.4 |
| | 100/150/40 | 100/200/40 | 150/200/40 | 150/300/40 | 200/250/40 | 200/400/40 | 250/300/40 | 250/500/40 |
| 0 | 53.9 | 51.9 | 52.5 | 49.3 | 101.1 | 51.0 | 46.3 | 46.1 |
| $10^1$ | 544.6 | 162.8 | 229.1 | 273.1 | 261.7 | 466.1 | 167.9 | 615.0 |
| $10^2$ | 659.5 | 759.0 | 776.8 | 649.8 | 689.9 | 565.1 | 720.9 | 584.1 |
| $10^3$ | 1270.0 | 1210.2 | 1189.5 | 1121.8 | 978.4 | 1046.9 | 1061.4 | 1057.1 |
| $10^5$ | 1824.8 | 1783.8 | 1666.5 | 1612.0 | 1486.8 | 1402.6 | 1311.3 | 1368.1 |
| $10^6$ | 1821.9 | 1751.6 | 1742.1 | 1544.9 | 1589.3 | 1397.1 | 1477.3 | 1419.6 |

All 3 microparticle concentrations were tested but only the data using 0.12% solids is shown above in Table 3 since this data was representative (as in Example 3) of that obtained with all 3 microparticle concentrations.

As shown by this example, when the concentration of the unlabeled primer was higher than, or equal to, the concentration of the labeled primer, a "hook effect" was observed. When the labeled primer was present at higher concentrations than the unlabeled primer the hook effect dissipated.

While the invention has been described in detail and with reference to specific embodiments, it will be apparent to one skilled in the art that various changes and modifications may be made to such embodiments without departing from the spirit and scope of the invention.

What is claimed is:

1. A method for amplifying and detecting a target nucleic acid in a test sample comprising the steps of:
   (a) forming an amplification mixture comprising a test sample, a first primer sequence and a second primer sequence, and amplifying agents,
   (b) amplifying the target sequence to generate copies of the target sequence comprising an amplification product from the first primer sequence and the second primer sequence, and
   (c) detecting the copies of the target sequence as an indication of the presence of the target nucleic acid sequence in the test sample,
   wherein the first primer sequence is present at a concentration between 100 nM and 250 nM, and the second primer sequence is present at a concentration of between 50 nM and 500 nM, and wherein the concentration of the first primer sequence and the second primer sequence differ by at least 15% and differ by no more than 250%, and
   wherein the presence of the target nucleic acid is indicated by the presence of an amplification product and amplification and detection are efficiently increased by avoiding plateauing of signals.

2. The method of claim 1 wherein the concentration of the first primer in the reaction is 20% to 150% greater than the concentration of the second primer.

3. The method of claim 1, wherein the second primer is labeled.

4. The method of claim 1, wherein the presence of the target nucleic acid is indicated by contacting the sample with a labeled probe specific for the target nucleic acid.

* * * * *

SEQUENCE LISTING

<160> NUMBER OF SEQ ID NOS: 4

<210> SEQ ID NO 1
<211> LENGTH: 2348
<212> TYPE: DNA
<213> ORGANISM: HIV-1

<400> SEQUENCE: 1

```
acagtattag taggacctac acctgtcaac ataattggaa gaaatctgtt gactcagctt      60
gggtgcactt taaattttcc cattagtcct attgaaactg taccagtaaa attaaagcca     120
ggaatggatg gcccaaaagt taaacaatgg ccattgacag aagaaaaaat aaaagcatta     180
atagaaattt gtacagaaat ggaaaaggaa gggaaaattt caaaaattgg gcctgaaaat     240
ccatacaata ctccagtatt tgccataaag aaaaaagaca gtactaaatg gagaaaatta     300
gtagatttca gagaacttaa taagaaaact caagacttct gggaagttca attaggaata     360
ccacatcctg cagggttaaa aaagaaaaaa tcagtaacag tactggatgt gggtgatgca     420
tatttttcag ttcccttaga taaagacttc aggaagtata ctgcatttac catacctagt     480
ataaacaatg aaacaccagg gattagatat cagtacaatg tgcttccaca gggatggaaa     540
ggatcaccag caatattcca aagtagcatg acaaaaatct tagagccttt tagaaaacaa     600
aatccagaca tagttatcta tcaatacatg gatgatttgt atgtaggatc tgacttagaa     660
atagggcagc atagagcaaa aatagaggaa ctgagacgac atctgttgag gtggggattt     720
accacaccag acaaaaaaca tcagaaagaa cctccattcc tttggatggg ttatgaactc     780
catcctgata aatggacagt acagcctata gtgctaccag aaaaagacag ctggactgtc     840
aatgacatac agaagttagt gggaaaattg aattgggcaa gtcagattta cgcagggatt     900
aaagtaaagc aattatgtaa actccttaga ggaaccaaag cactaacaga agtaatacca     960
ctaacagaag aagcagagct agaactggca gaaaacaggg aaattctaaa agaaccagta    1020
```

-continued

```
catggagtgt attatgaccc atcaaaagac ttaatagcag aagtacagaa gcaggggcaa      1080
ggccaatgga catatcaaat ttatcaagag ccatttaaaa atctgaaaac aggcaaatat      1140
gcaagaatga ggggtgccca cactaatgat gtaaaacaat taacagaggc agtgcaaaaa      1200
atagccacag aaagcatagt aatatgggga aagactccta aatttagact acccatacaa      1260
aaagaaacat gggaaacatg gtggacagag tatacgtaag ccacctggat tcctgagtgg      1320
gaggttgtca ataccoctcc cttagtgaaa ttatggtacc agttagagaa agaacccata      1380
gtaggtgcag aaactttcta tgtagatggg gcagctaaca gggagactaa aaaggaaaa      1440 gcaggatatg ttactaacag aggaagacaa aaggttgtct ccctaactga cacaacaaat      1500
cagaagactg agttacaagc aattcatcta gctttgcaag attcagggtt agaagtaaac      1560
atagtaacag actcacaata tgcattagga atcattcaag cacaaccaga taaaagtgaa      1620
tcagagttag tcagtcaaat aatagagcag ttaataaaaa aggaaaaggt ctatctggca      1680
tgggtaccag cacacaaagg aattggagga aatgaacaag tagataaatt agtcagtgct      1740
ggaatcagga aagtactatt tttagatgga atagataagg cccaagaaga ccatgagaaa      1800
tatcacagta attggagagc aatggctagt gactttaacc taccacctat agtagcaaaa      1860
gaaatagtag ccagctgtga taatgtcag ctaaaggag aagccatgca tggacaagta      1920
gactgtagtc caggaatatg gcaactagat tgtacacatt tagaaggaaa agttatcctg      1980
gtagcagttc atgtagccag tggatacata gaagcagaag ttattccagc agagacaggg      2040
caggagacag catactttct cttaaaatta gcaggaagat ggccagtaaa aacaatacat      2100
acagacaatg gccccaattt caccagtact acggttaagg ccgcctgttg gtggacggga      2160
atcaagcagg aatttggcat tccctacaat ccccaaagtc aaggagtaat agaatctatg      2220
aataaagaat taagaaaat tataggacag gtaagagatc aggctgaaca tcttaagaga      2280
gcagtacaaa tggcagtatt catccacaat tttaaaagaa aagggggat tgggggtac      2340 agtgcagg                                                              2348
```

<210> SEQ ID NO 2
<211> LENGTH: 29
<212> TYPE: DNA
<213> ORGANISM: Artificial Sequence
<220> FEATURE:
<223> OTHER INFORMATION: Unlabeled Primer

<400> SEQUENCE: 2

```
attccctaca atccccaaag tcaaggagt                                         29
```

<210> SEQ ID NO 3
<211> LENGTH: 22
<212> TYPE: DNA
<213> ORGANISM: Artificial Sequence
<220> FEATURE:
<223> OTHER INFORMATION: Labeled Primer

<400> SEQUENCE: 3

```
cctgcactgt accccccaat cc                                               22
```

<210> SEQ ID NO 4
<211> LENGTH: 18
<212> TYPE: DNA
<213> ORGANISM: Artificial Sequence
<220> FEATURE:
<223> OTHER INFORMATION: Probe

```
-continued

<400> SEQUENCE: 4
acagcagtac aaatggca                                                       18
```